United States Patent [19]

Casagrande et al.

[11] Patent Number: 4,983,606

[45] Date of Patent: Jan. 8, 1991

[54] PHARMACEUTICALLY-ACTIVE PHTHALAZINE COMPOUNDS

[75] Inventors: Cesare Casagrande, Arese; Francesco Santangelo, Milan, both of Italy

[73] Assignee: Zambon Group S.p.A., Vicenza, Italy

[21] Appl. No.: 256,560

[22] Filed: Oct. 12, 1988

[30] Foreign Application Priority Data

Oct. 12, 1987 [IT] Italy ................................. 22218 A/87

[51] Int. Cl.[5] .................. C07D 237/32; C07D 401/06; C07D 403/06; A61K 31/50
[52] U.S. Cl. ..................................... 514/248; 544/237
[58] Field of Search .......................... 544/237; 514/248

[56] References Cited

U.S. PATENT DOCUMENTS 4,134,980 1/1979 Eberlein ................................ 544/237

Primary Examiner—Mark L. Berch
Attorney, Agent, or Firm—Cushman, Darby & Cushman

[57] ABSTRACT

Compounds having the formula

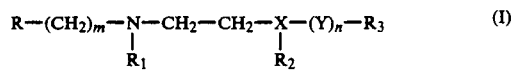

wherein R is 2-[1-oxo-(2H)-phthalazinyl], $R_1$, $R_2$, $R_3$, $R_4$, $R_5$, $R_6$, X, Y, m and n have the meanings shown in the description. The compounds of formula I are pharmaceutically active as anti-vasospastic, anti-aggregating, and anti-proliferative agents.

7 Claims, No Drawings

PHARMACEUTICALLY-ACTIVE PHTHALAZINE COMPOUNDS

The present invention relates to compounds containing a substituted phthalazine ring, their use in the pharmaceutical field and the pharmaceutical compositions containing them. An object of the present invention are the compounds containing a substituted phthalazine ring of the formula:

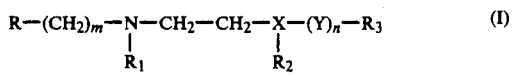
(I)

wherein
R is a 2-[1-oxo-(2H) phthalazinyl] group of formula

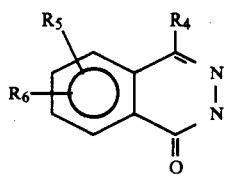

where $R_4$ is hydrogen or $C_1$-$C_4$ alkyl;

$R_5$ and $R_6$, equal to or different from one another, are hydrogen, halogen, nitro, $C_1$-$C_4$ alkyl or $C_1$-$C_4$ alkoxy;

$R_1$ and $R_2$ independently are $C_1$-$C_4$ alkyl or together are a —$CH_2$—$CH_2$— group;

X is nitrogen or CH;

Y is selected from —$CH_2$—, —CO—, —CHOH— and —NH—CO—.

$R_3$ is a phenyl optionally substituted by one to three substitutents selected from halogen $C_1$-$C_4$ alkyl and $C_1$-$C_4$ alkoxy;

m is an integer from 1 to 4;

n is zero or 1;

and its salts with pharmaceutically acceptable acids.

The compounds of formula I are endowed with anti-vasospastic, anti-aggregating and anti-proliferative activity and are useful in the pharmaceutical field.

Specific compounds of formula I are:

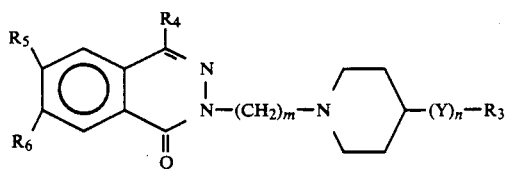
(I-A)

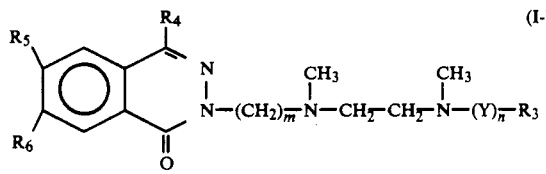
(I-B)

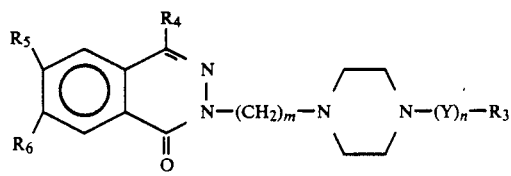
(I-C)

In the above formulae $R_3$, $R_4$, $R_5$, $R_6$, Y, m and n have the meanings mentioned with regard to formula I. Having regard to their pharmacological activity the preferred compounds are the compounds of formulas I-A, I-B and I-C wherein $R_4$ is hydrogen, n is 1 and Y is —CO— or —CHOH—; among these compounds even more preferred are those in which $R_3$ is 4-fluoro-phenyl and those wherein m is 2 or 3.

The preparation of the compounds of formula I is performed by condensing a compound of the formula

(II)

(wherein R and m have the meanings mentioned with regard to formula I and Z is chlorine, bromine, iodine, arylsulfonyloxy or alkylsulfonyloxy group) with an amine of the formula

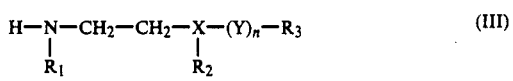
(III)

(wherein $R_1$, $R_2$, $R_3$, X, Y and n have the meanings mentioned with regard to formula I).

The reaction is carried out in an inert solvent, in the presence of a base and at from 0° C. to the boiling temperature of the reaction mixture.

Examples of suitable solvents are hydrocarbons, halogen-substituted hydrocarbons, aliphatic and alicyclic ethers, esters, nitriles, amides and tertiary amines.

Examples of preferred solvents are methylene chloride, tetrahydrofurane, ethyl acetate, acetonitrile, dimethylformamide and pyridine.

Examples of suitable bases are the alkaline carbonates or bicarbonates and the tertiary amines such as pyridine and triethylamine.

When a tertiary amine is used as solvent it is not necessary to use any other base.

The compound of formula III can be used in excess and can act either as a solvent or as a base.

The reaction rate of the condensation step may be increased by adding to the reaction mixture a catalytic amount of an alkaline iodide.

The compounds of formula II are known or may be easily prepared according to known methods (Kolesnikov V., Bisagni E.,—Chimie Thérapeutique, 2, 250–3, 1967) for example by reacting a benzoic acid of the formula

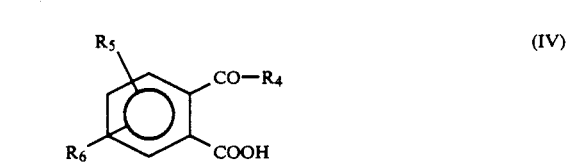
(IV)

(wherein $R_4$, $R_5$ and $R_6$ have the meanings mentioned with regard to formula I) with a hydroxy alkyl hydrazine having the formula

(V)

(wherein m has the meaning mentioned with regard to formula I). This reaction is carried out simply by mixing the reactants in an inert solvent at room temperature.

By means of such a condensation the compounds having the following formula are obtained

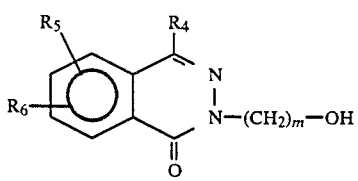

(wherein R4, R5, R6 and m have the meanings mentioned with regard to formula I).

The substitution of the hydroxy group in the branched chain of the compounds VI with chlorine or bromine or its transformation into an arylsulfonyloxy or alkylsulfonyloxy group gives the compounds of formula II.

The substitution reaction may be carried out by treatment with hydrogen chloride, bromide or iodide, with organic or inorganic acid halides such as oxalyl chloride, thionyl chloride, phosphorus bromide or with triphenylphosphite followed by reaction with hydrogen halides or with halogens.

The preparation of the compounds of formula II wherein Z is alkylsulfonyloxy or arylsulfonyloxy is carried out by acylation of the compounds of formula VI with alkyl- or aryl-sulfonic acid halides in an inert solvent, in the presence of a base and at from −30° C. to the boiling temperature of the reaction mixture.

The amines of formula III are known or may be easily prepared according to known methods. Specific examples of such compounds are 4-(4-fluorobenzoyl)-piperidine
4-(4-chlorobenzoyl)-piperidine
4-(4-methylbenzoyl)-piperidine
4-(3,4,5-trimethoxybenzoyl)-piperidine
1-(4-fluorobenzoyl)-piperazine
1-(4-chlorobenzoyl)-piperazine
4-phenyl-piperidine
4-benzyl-piperidine
1-phenyl-piperazine
1-benzyl-piperazine
4-(4-fluorophenyl)-piperidine
1-(4-fluorophenyl)-piperazine
N1, N2-dimethyl-N2-(4-fluorobenzoyl)-ethylenediamine
N1, N2-dimethyl-N2-(3,4,5-trimethoxybenzoyl)-ethylenediamine
N1, N2-dimethyl-N2-benzyl-ethylenediamine
1-(4-fluorophenyl)-2-methyl-4-methylamine-butan-1-one The compounds of formula I wherein Y is —CHOH— are preferably prepared by reduction of the corresponding compounds of formula I wherein Y is —CO—.

The preparation of the salts of the compounds of formula I is carried out by reaction of the compound of formula I with the selected pharmaceutically-acceptable organic or inorganic acid. Examples of such acids are hydrogen chloride, bromide, iodide, and acetic, benzoic, nitric, sulphuric, phosphoric, maleic, fumaric, succinic, aspartic, tartaric, methanesulfonic and benzenesulfonic acid.

As mentioned above the compounds of formula I are endowed with anti-vasospastic, anti-aggregating and anti-proliferative activity and are therefore useful in the treatment of cardiovascular and tumoral diseases.

For pharmaceutical use the compounds of formula I are preferably used in the form of a suitable pharmaceutical composition.

Such compositions contain the active ingredient (a compound of formula I or a salt thereof) together with a pharmaceutical excipient suitable for oral, rectal or parenteral administration.

The compositions may be prepared in a solid form such as tablets, pills, capsules, granules and slow-release solid forms, in a semi-solid form such as suppositories, in a liquid form such as solutions, suspensions or emulsions.

As usual, the compositions will contain additives suitable for pharmaceutical use selected among preservatives, stabilizers, emulsifiers, salts for regulating osmotic pressure, buffers, flavouring and colouring agents and the like.

If special therapies so require it is possible to associate in the compositions of this invention other compatible active ingredients whose simultaneous administration is therapeutically useful.

The dose of the compound of formula I to be administerd to the patient varies in relation to different factors such as the specific therapy, the selected administration route and the corresponding type of composition as well as the specific compound of formula I which is used.

The daily dose will, in general, range from 0.01 to 50 mg/kg, preferably from 0.1 to 10 mg/kg, and will be administered in a single dose or in doses repeated at appropriate intervals. The following examples illustrate the invention without limiting it.

EXAMPLE 1

Preparation of 2-(2-hydroxyethyl)-6,7-dimethoxy-1(2H)-phthalazinone

To a solution of 6-formil-3,4-dimethoxy-benzoic acid (21 g; 0.1 mole) in absolute ethyl alcohol (200 ml) 2-hydroxy-ethyl hydrazine (8.35 g, 0.11 mole) is added. The mixture is stirred for 30 minutes at room temperature, then is cooled to 0° C. and, after dilution with ethyl ether, 2-(2-hydroxyethyl)-6,7-dimethoxy-1(2H)-phthalazinone is separated by filtration (m.p. 174°–176° C.).

EXAMPLE 2

Preparation of 2-(2-chloroethyl)-6,7-dimethyoxy-1(2H)-phthalazinone

To a solution of 2-(2-hydroxyethyl)-6,7-dimethoxy-1(2H)-phthalazinone (2.5 g; 0.01 mole) obtained as described in Example 1, in chloroform (50 ml) thionyl chloride (12.9 ml) is added and the mixture is kept under stirring for 60 minutes. The solvent is evaporated under reduced pressure and the residue is crystallized from toluene/ethyl ether; 2-(2-chloroethyl)-6,7-dimethoxy-1(2H)-phthalazinone is obtained (m.p. 181°–183° C.).

EXAMPLE 3

Preparation of 2-{2-[4-phenylpiperazin-1-yl]-ethyl}-6,7-dimethoxy-1(2H)-phthalazinone dihydrochloride A mixture of 2-(2-chloroethyl)-6,7-dimethoxy-1(2H)-phthalazinone (2.68 g; 0.01 mole) obtained as described in Example 2, N-phenyl piperazin (1.5 ml), triethyl amine (2.78 ml) and potassium iodide (0.16 g; 0,001 mole) in acetonitrile (50 ml), is refluxed for 12 hours.

The solvent is evaporated under reduced pressure and the residue is dissolved in dilute HCl, washed with methylene chloride and after alkalinization with NaHCO$_3$, the mixture is extracted with methylene chloride, dried on sodium sulphate, filtered and evaporated. The residue is dissolved in acetone, made acid with HCl in ethyl ether and the product which separates is filtered and recrystallized from 95% ethanol to give 2-[2-(4-phenylpiperazin-1-yl)-ethyl]-6,7-dimethoxy-1(2H)-phthalazinone dihydrochloride (m.p. 222°–226° C.).

EXAMPLE 4

Preparation of 2-[2-(4-benzylpiperazin-1-yl)-ethyl]-6,7-dimethyoxy-1(2H)-phthalazinone dihydrochloride Working as described in Example 3 but replacing N-phenyl piperazine with an equivalent amount of N-benzyl piperazine, 2-[2-(4-benzylpiperazin-1-yl)-ethyl]-6,7-dimethoxy-1(2H)-phthalazinone dihydrochloride is obtained (m.p. 252°–255° C., from ethyl alcohol).

EXAMPLE 5

Preparation of 2-[2-(4-benzamidopiperidin-1-yl)-ethyl]-6,7-dimethoxy-1(2H)-phthalazinone hydrochloride Working as described in Example 3 but replacing N-phenyl piperazin with an equivalent amount of 4-benzamido-piperidine, 2-[2-(4-benzamidopiperidin-1-yl)-ethyl]-6,7-dimethoxy-1(2H) phthalazinone hydrochloride is obtained (m.p. 242°–244° C., from acetone).

EXAMPLE 6

Preparation of 2-{2-[4-(4-fluorobenzoyl)-piperidin-1-yl]-ethyl}-6,7-dimethoxy-1(2H)-phthalazinone hydrochloride Working as described in Example 3 but replacing N-phenyl piperazine with an equivalent amount of 4(4-fluorobenzoyl)-piperidine and purifying the resulting product by silica-gel column chromatography (eluent: methylene chloride/methyl alcohol = 98/2) 2-{2-[4-(4-fluorobenzoyl)-piperidin-1-yl]-ethyl}-6,7-dimethoxy-1(2H)-phthalazinone hydrochloride is obtained (m.p. 255°–260° C., from methylene chloride/methyl alcohol).

EXAMPLE 7

Preparation of 2-[2-(4-benzylpiperidin-1-yl)-ethyl]-6,7-dimethoxy-1(2H)-phthalazinone hydrochloride Working as described in Example 3 but replacing N-phenyl piperazin with an equivalent amount of 4-benzylpiperidine, 2[2-(4-benzylpiperidin-1-yl)-ethyl]-6,7-dimethoxy-1(2H)-phthalazinone hydrochloride is obtained (m.p. 213°–215° C., from acetone/ethyl ether).

EXAMPLE 8

Preparation of 2-[2-(N-3,4,5-trimethoxybenzoyl)-N,N'-dimethylethylenediamino]-ethyl]-6,7-dimethoxy-1(2H)-phthalazinone hydrochloride Working as described in Example 3 but replacing N-phenyl piperazin with an equivalent amount of N-(3,4,5-trimethoxybenzoyl)-N,N'-dimethylethylenediamine, 2-[2-(N-3,4,5-trimethoxybenzoyl)-N,N'-dimethylethylenediamino]-ethyl]-6,7-dimethoxy-1(2H)-phthalazinone hydrochloride is obtained (m.p. 201°–204° C., from isopropyl alcohol).

EXAMPLE 9

Preparation of 2-{2-[4-(4-fluorobenzoyl)-piperidin-1-yl]ethyl}-1(2H)-phthalazinone hydrochloride Working as described in Example 3 but replacing 2-[2chloroethyl]-6,7-dimethoxy-1(2H)-phthalazinone with an equivalent amount of 2-(2-chloroethyl)-1(2H)-phthalazinone and replacing N-phenyl piperazine with an equivalent amount of 4-(4-fluorobenzoyl)-piperidine, 2-{2-[4-(4-fluorobenzoyl)-piperidin-1-yl]-ethyl}-1(2H)-phthalazinone hydrochloride is obtained (m.p. 230°–250° C., from ethyl alcohol/ethyl ether).

EXAMPLE 10

Preparation of 2-{2-[4-(4-fluorobenzoyl)-piperidin-1-yl]-ethyl}-7-nitro-1(2H)-phthalazinone hydrochloride Working as described in Example 3 but replacing 2-[2-chloroethyl]-6,7-dimethoxy-1(2H)-phthalazinone with an equivalent amount of 2-(2-chloroethyl)-7-nitro-1(2H)-phthalazinone and replacing N-phenyl piperazine with an equivalent amount of 4-(4-fluorobenzoyl)-piperidine, 2-{2-[4-(4-fluorobenzoyl)-piperidin-1-yl]-ethyl}-7-nitro-1-(2H)-phthalazinone hydrochloride is obtained (m.p. 280°–285° C., from ethyl alcohol).

EXAMPLE 11

Preparation of 2-{2-[4-(4-fluoro-alpha-hydroxybenzyl)-piperidin-1-yl]-ethyl}-6,7-dimethoxy-1(2H)-phthalazinone hydrochloride To a solution of 2-{2-[4-(4-fluorobenzoyl)-piperidin-1-yl]ethyl}-6,7-dimethoxy-1(2H)-phthalazinone (1.5 g; 0,0034 mole) (obtained from the corresponding hydrochloride described in Example 6, after suspension in water, neutralization with ammonium hydroxide and extraction of the base with chloroform, which is anhydrified on sodium sulphate and dry evaporated) in methyl alcohol (30 ml), sodium boron hydride (0.396 g, 0.01 mole) is added at room temperature and the mixture is kept under stirring for 12 hours. The solvent is evaporated at reduced pressure and the residue, dissolved in dilute HCl, is washed with methylene chloride and made alkaline with sodium bicarbonate, then is extracted with methylene chloride, dried on sodium sulphate, filtered and evaporated.

The product is dissolved in methyl alcohol and the solution is acidified with ethyl ether saturated with HCl, the precipitate which separates is crystallized from ethyl alcohol/acetone, 2-{2-[4-(4-fluoro-alpha-hydroxybenzyl)-piperidin-1-yl]ethyl}-6,7-dimethoxy-1-(2H)-phthalazinone hydrochloride is thus obtained (m.p. 200°–204° C.).

EXAMPLE 12

Preparation of 2-[3-(hydroxypropyl)-6,7-dimethoxy-1(2H)-phthalazinone

Working as described in Example 1 but replacing 2-hydroxyethyl hydrazine with an equivalent amount of 3-hydroxypropyl hydrazin, 2-[3-(hydroxypropyl)-6,7-dimethoxy-1(2H)-phthalazinone is obtained (m.p. 178° C., from ethyl alcohol/ethyl ether).

EXAMPLE 13

Preparation of 2-(3-chloropropyl)-6,7-dimethoxy-1(2H)-phthalazinone

Working as described in Example 2 but replacing 2-(2-hydroxyethyl)-6,7-dimethoxy-1(2H)-phthalazinone with an equivalent amount of 2-(3-hydroxypropyl)-6,7-dimethoxy-1(2H)-phthalazinone obtained as described in Example 12, 2-(3-chloropropyl)-6,7-dimethoxy-1(2H)-phthalazinone is obtained (m.p. 185°–187° C., from chloroform/ethyl ether).

EXAMPLE 14

Preparation of 2-{3-[4-(4-fluorobenzoyl)-piperidin-1-yl]propyl]-6,7-dimethoxy-1(2H)-phthalazinone hydrochloride Working as described in Example 3 but replacing 2-(2-chloroethyl)-6,7-dimethoxy-1(2H)-phthalazinone with an equivalent amount of 2-(3-chloropropyl)-6,7-dimethoxy-1(2H)-phthalazinone obtained as described in Example 13, and replacing N-phenylpiperazine with an equivalent amount of 4-(4-fluorobenzoyl)-piperazine, 2-{3-[4-(4-fluorobenzoyl)-piperidin-1-yl]-propyl}-6,7-dimethoxy-1(2H)-phthalazinone hydrochloride is obtained (m.p. 250°–252° C., from ethyl acetate).

We claim:

1. A compound of the formula

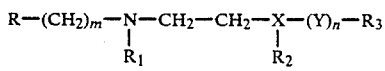

wherein

R is a 2-[1-oxo-(2H)-phthalazinyl] group formula

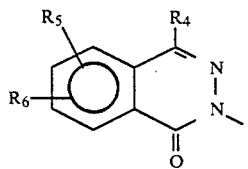

wherein $R_4$ is hydrogen;

$R_5$ and $R_6$, equal to or different from one another, are hydrogen, halogen, nitro, $C_1$-$C_4$ alkyl or $C_1$-$C_4$ alkoxy;

$R_1$ and $R_2$, independently, are $C_1$-$C_4$ alkyl or together are —$CH_2$—$CH_2$— group;

X is nitrogen or —CH—;

Y is selected from —CO— and —CHOH—.

$R_3$ is phenyl optionally substituted by one to three substituents selected from halogen, $C_1$-$C_4$ alkyl and $C_1$-$C_4$ alkoxy;

m is an integer from 1 to 4;

n is 1; and its salts with pharmaceutically acceptable acids.

2. A compound of the formula

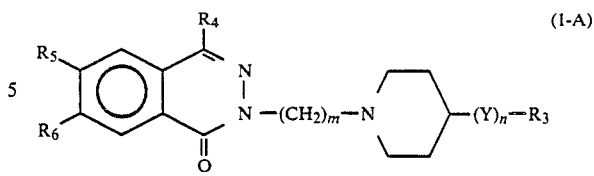

wherein $R_4$ is hydrogen or $C_1$-$C_4$ alkyl;

$R_5$ and $R_6$, equal to or different from one another, are hydrogen, halogen, nitro, $C_1$-$C_4$ alkyl or $C_1$-$C_4$ alkoxy;

Y is selected from —$CH_2$, —CO—, —CHOH— and —NH—CO—.

$R_3$ is phenyl optionally substituted by one to three substituents selected from halogen, $C_1$-$C_4$ alkyl and $C_1$-$C_4$ alkoxy;

m is an integer from 1 to 4;

n is zero or 1.

3. A compound having the formula

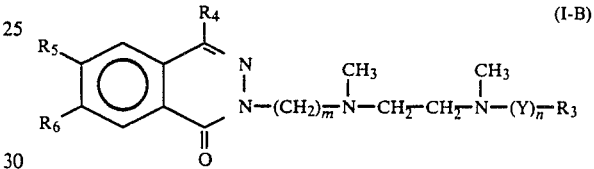

wherein $R_4$ is hydrogen or $C_1$-$C_4$ alkyl;

$R_5$ and $R_6$, equal to or different from one another, are hydrogen, halogen, nitro, $C_1$-$C_4$ alkyl or $C_1$-$C_4$ alkoxy;

Y is selected from —$CH_2$—, —CO—, —CHOH— and —NH—CO—.

$R_3$ is a phenyl optionally substituted by one to three substituents selected from halogen, $C_1$-$C_4$ alkyl and $C_1$-$C_4$ alkoxy;

m is an integer from 1 to 4;

n is zero or 1; and its salts with pharmaceutically acceptable acids.

4. A compound of the formula

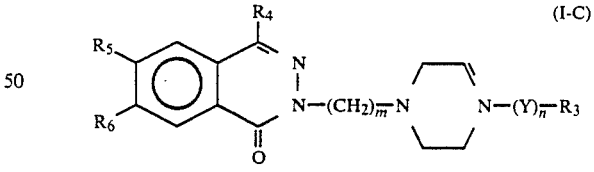

wherein $R_4$ is hydrogen or $C_1$-$C_4$ alkyl;

$R_5$ and $R_6$, equal to or different from one another, are hydrogen, halogen, nitro, $C_1$-$C_4$ alkyl or $C_1$-$C_4$ alkoxy;

Y is selected from —$CH_2$, —CO—, —CHOH— and —NH—CO—.

$R_3$ is phenyl optionally substituted by one to three substituents selected from halogen, $C_1$-$C_4$ alkyl and $C_1$-$C_4$ alkoxy;

m is an integer from 1 to 4;

n is zero or 1.

5. A pharmaceutical composition having anti-vasospastic, platelet anti-aggregating and tumor anti-proliterative properties comprising a therapeutically effective amount of a compound according to claim 2, and one or more pharmaceutically acceptable excipients.

6. A compound of the formula

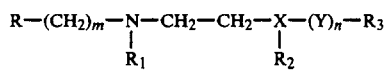

wherein

R is a 2-[1-oxo-(2H)-phthalazinyl] group of formula

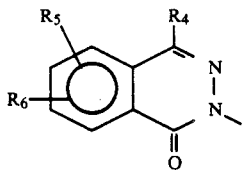

wherein $R_4$ is hydrogen or $C_1$-$C_4$ alkyl,
$R_5$ and $R_6$, equal to or different from one another, are hydrogen, halogen, nitro, $C_1$-$C_4$ alkyl or $C_1$-$C_4$ alkoxy; $R_1$ and $R_2$, independently, are $C_1$-$C_4$ alkyl or together are —$CH_2$—$CH_2$— group;
X is nitrogen or —CH—;
Y is selected from —$CH_2$—, —CO—, —CHOH— and —NH—CO—.
$R_3$ is fluorophenyl;
m is 2 or 3;
n is zero or 1;
and its salts with pharmaceutical acceptable acids.

7. A pharmaceutical composition according to claim 5 in a suitable dosage unit wherein the daily dosage will be in the range of 0.01 to 50 mg/kg.